United States Patent [19]

Mallo et al.

[11] Patent Number: 5,053,460

[45] Date of Patent: Oct. 1, 1991

[54] HYDROPHILIC POLYMER BASED ON ACRYLIC ACID AND ALKALI METAL ACRYLATE, ITS PREPARATION PROCESS AND ITS USE AS AN ABSORBING AGENT

[75] Inventors: Paul Mallo, Rueil Malmaison; Marie-Thérèse Moreau, Saint Brice sous Foret; Jean Cabestany, Stains, all of France

[73] Assignee: Societe Francaise Hoechst, Puteaus, France

[21] Appl. No.: 494,366

[22] Filed: Mar. 16, 1990

[30] Foreign Application Priority Data

Mar. 16, 1989 [FR] France ................. 89 03488

[51] Int. Cl.$^5$ ................................. C08F 8/00
[52] U.S. Cl. ..................... 525/116; 525/119
[58] Field of Search .................. 525/116, 119

[56] References Cited

U.S. PATENT DOCUMENTS

| | | |
|---|---|---|
| 4,552,938 | 11/1985 | Mikita et al. |
| 4,654,393 | 3/1987 | Mikita et al. |
| 4,703,067 | 10/1987 | Mikita et al. |
| 4,818,796 | 4/1989 | Das et al. |

FOREIGN PATENT DOCUMENTS

| | | |
|---|---|---|
| 0295784 | 12/1988 | European Pat. Off. |
| 3239476 | 5/1983 | Fed. Rep. of Germany |
| 2606414 | 5/1988 | France |

*Primary Examiner*—Bernard Lipman
*Attorney, Agent, or Firm*—Browdy and Neimark

[57] ABSTRACT

Hydrophilic polymer, as microbeads insoluble in water, based on acrylic acid and an alkali metal acrylate constituted by an acrylic acid - potassium acrylate copolymer, cross-linked with 100 ppm to 3,000 ppm relative to the total weight of monomers of one or more cross-linking agents chosen from the group constituted by the products of general formula I:

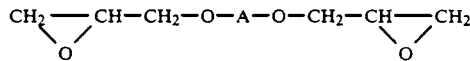

$A$ = a bivalent radical derived from a $C_3$–$C_6$ alkane presenting an absorption capacity for a salty physiological solution of 30 to 70 g per gram and from 10 to 35 g per gram under pressure, preparation process and use notably in articles of hygiene.

9 Claims, No Drawings

HYDROPHILIC POLYMER BASED ON ACRYLIC ACID AND ALKALI METAL ACRYLATE, ITS PREPARATION PROCESS AND ITS USE AS AN ABSORBING AGENT

The present invention relates to a hydrophilic polymer with a high absorption capacity for saline aqueous solutions, based on acrylic acid and alkali metal acrylate, its preparation process and its application as an absorbing agent, notably as an absorbing agent for babies, nappies, i.e. diapers.

Polymer substances capable of absorbing several times their own weight of water and converting it into a gel are known. These hydrophilic polymers are either natural or semi-synthetic polymers such as derivatives of cellulose, starch, alginate, polysaccharides, or synthetic polymers based notably on maleic acid or (meth)acrylic acid.

Thus a large variety of hydrophilic polymers are known, but for agricultural, horticultural or sanitary use, products are always being sought which offer an increased absorption capacity not only for water, but also for water charged with electrolytes, with a rapid speed of absorption and good powers of retention in the gel state.

Moreover, for hygienic use, notably in the manufacture of objects intended to be in contact, in a damp state, with human skin, products are sought that are atoxic, of low cost, do not present syneresis, contain neither nitrated derivatives nor residual monomers and simultaneously possess an increased absorption capacity both unloaded and loaded with saline aqueous solutions. In effect, for example, one of the important problems to resolve in the manufacture of diapers is the retention of urine, for several hours, at temperatures that may reach 40° C. and despite the pressure caused by the baby's weight. A partial solution to these problems has been provided by the teaching of European Patent No. 0,083,022 which recommends a post-cross-linking of the water-absorbing resin with a cross-linking agent having at least two functional groups which can react with the carboxylate groups or the groups present in this carboxylate-group resin, such as hydroxyl, amino or sulpho groups in the presence of 0.01 to 1.3 parts by weight of water per part by weight of resin. This solution, though interesting, is expensive to employ: it requires, in effect, the preparation in a first stage of the water-absorbing resin, and then in a second stage the subjection of this resin to a post-cross-linking under particular conditions.

In conclusion, it can be said that today no known hydrophilic polymers absorbing salty water respond to the needs expressed by the market.

Now the Applicant has surprisingly discovered such a product. The present invention therefore relates to a hydrophilic polymer, in the form of microbeads insoluble in water, based on acrylic acid and alkali metal acrylate, characterised in that it is composed of a potassium acrylate-acrylic acid copolymer, containing, in molar proportions, from 55 to 85% of potassium acrylate, cross-linked with from 100 ppm to 3,000 ppm relative to the total weight of monomers of one or more cross-linking agents chosen from the group constituted by the products of general formula I:

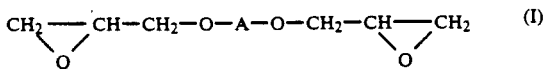

in which A represents a bivalent radical derivative of a $C_3$–$C_6$ alkane branched or not, by the removal of a hydrogen atom from each of the two terminal carbon atoms such as the following radicals; trimethylene, tetramethylene, ethylethylene, propylene, 2,2-dimethyl-1,-3 propanediyl, and that it presents an absorption capacity for a salty physiological solution of the order of 30 to 70 g per gram and of the order of 10 to 35 g per gram under a pressure of 15 g per $cm^2$.

By "microbeads", one means approximately spherical beads of a diameter of between 0.05 and 1 mm.

By "insoluble in water", one means that the polymers contain, at ambient temperature, less than 5% of products soluble in water.

These copolymers are preferably cross-linked with 200 to 3,000 ppm and notably 200 to 1,000 ppm relative to the weight of the monomers of bis(oxiranylmethoxy)-1,4-butane, currently designated 1,4-butanediol diglycidyether.

Among the copolymers defined above, more particularly the acrylic acid-potassium acrylate copolymers containing in molar proportions from 65 to 80% of potassium acrylate may be cited.

By "salty physiological solution" one designates an isotonic solution containing 9 g of sodium chloride per liter of distilled water.

According to the invention, the copolymers defined above are able to be prepared by a polymerisation process in a water-in-oil suspension carried out in an inert atmosphere, characterised in that an aqueous phase containing the cross-linking agent or agents of general formula (I), one or more hydrosoluble polymerisation initiators which generate free radicals, the chosen monomers and water in a quantity such that the monomer concentration is 55±10% by weight are introduced slowly, with agitation, into the deoxygenated oil phase, maintained at boiling point and containing a colloid protector, then when the polymerisation reaction is finished, 75 to 90% of the water introduced is eliminated by azeotropic distillation and then the polymer formed is isolated, either by filtration followed by drying at 110°±10° C. for at least 30 minutes, or by direct azeotropic drying at 110°±10° C. for at least 30 minutes in such a manner so as to obtain micropearls of the sought hydrophilic polymer containing 7±3% of water by weight.

According to a variation of the process described above, the cross-linking agent or agents of general formula (I) used can be placed in total or in part in the oil phase.

By "deoxygenated oil", one means a virtually perfectly or preferably perfectly deoxygenated oil.

The oil phase is principally constituted by one or more hydrocarbons, non-miscible with water, inert with respect to the polymerisation initiators and able to produce an azeotrope with water, such as cyclohexane or petrol fractions with boiling points of between 50° and 180° C.

The ratio by weight of the oil phase to the aqueous phase is advantageously between 0.9 and 1.1.

The polymerisation reaction is conducted under reflux of the reaction medium, usually at ambient pressure. It can equally be achieved at a lower or higher pressure to that of ambient pressure.

Preferably the colloid protector used at a dosage of 0.5 to 2% by weight relative to the weight of the monomers is chosen from among those currently used in this type of polymerisation in suspension (cf Kirk-Othmer, Encyclopaedia of Chemical Technology, 3rd edition, volume 1. page 400). Advantageously, one will chose a cellulose ether and, preferably, a cellulose ethylether presenting an ethoxyl proportion of 48 to 49.5% (cf Encyclopaedia of Polymer Science and Engineering, 2nd edition, volume 3, page 254). The colloid protector is dissolved or dispersed beforehand in the oil phase.

The polymerisation reaction is started with one or more hydrosoluble free radical generators, offering a half-life at 70° C. greater than two hours. Advantageously, the polymerisation reaction is initiated with a mixture of at least two different hydrosoluble initiators such as defined previously of which at least one is chosen from among the mineral peroxides, and at least one is chosen from among the azo-compound derivatives. They are advantageously used at the concentration of 200 ppm to 3,000 ppm relative to the weight of the monomers and advantageously from 500 to 1,000 ppm. Such initiating agents are notably certain mineral peroxides such as sodium peroxodisulphate or certain azo-compounds such as 4,4'-dicyano-4,4'-azo- dipentanoic acid. The initiating agent or agents used are dissolved in the water then this solution is carefully deoxygenated.

The potassium acrylate is advantageously obtained in aqueous solution, by direct salification of an aqeous solution of acrylic acid with potash. This salification is advantageously effected at a temperature of between 20° and 35° C. The monomers used are dissolved in the water, preferably at a concentration of approximately 55±10% by weight.

The aqueous solution of initiator or initiators and the aqueous medium containing the monomers in solution, and optionally the chosen cross-linking agent or agents, are advantageously introduced into the oil phase after extemporaneously mixing during their introduction, in such a manner that they only remain in contact for a few seconds.

The duration of the introduction can vary according to the operating units, but generally it is comprised between one and two hours. At the end of the introduction it is advantageous to maintain the reaction medium at boiling point under agitation so as to perfect the polymerisation.

During the polymerisation reaction, the copolymers formed spontaneously cross-link with each other to produce cross-linked copolymers insoluble in water, of high hydrophilic power and with a very low proportion of residual monomers, which are always lower than 0.01% by weight relative to the weight of polymer.

The spontaneous cross-linking is accordingly more favoured the lower the degree of neutralisation of the acrylic acid and the higher the polymerisation temperature. The copolymers of the present invention are thus cross-linked, on the one hand by thermal means and on the other, by chemical means by the cross-linking agent or agents of general formula (I).

In order to develop all its properties, the hydrophilic polymer according to the present invention should be dried for at least 30 minutes at a temperature of 110°±10° C., in such a way so as to obtain a homogeneous drying even in the interior of the beads.

It is very surprising that a hydrophilic polymer presents with respect to salty water a high absorption capacity, just as well as under the influence of a pressure of 15 g/cm$^2$, for a person skilled in the art, these two properties are antinomic. It is in effect known that to obtain a hydrophilic polymer presenting a high absorption capacity vis-a-vis salty water under pressure, this polymer must be highly cross-linked, in order not to be crushed and, reciprocally, a high absorption capacity in a state such as is obtained with a very weakly cross-linked polymer. Now the hydrophilic polymers of the present invention simultaneously possess these two properties, which indicates that the microbeads of the polymer are weakly cross-linked at the centre and highly cross-linked at the surface. One could therefore say that the micropearls of the polymers according to the present invention present a "core-shell" structure.

The water absorption capacity of the polymer is determined at 20° C., by agitating for 30 minutes 0.4 g of polymer in 500 g of water, then by weighing the drained polymer gel. The weight found is related to 1 g of polymer. The copolymers of the present invention show in this test an absorption capacity of the order of 250 to 750 g per gram.

The salty physiological solution absorption capacity of the polymer is determined at 20° C., by agitating for 30 minutes 2 g of polymer in 500 g of salty physiological solution, then by weighing the drained polymer gel obtained. The weight found is related to 1 g of polymer, as previously. The copolymers of the present invention show in this test an absorption capacity of the order of 30 to 70 g per gram.

The speed of absorption of a salty physiological solution by the polymer is determined at 20° C., in a 100 ml beaker, with a diameter of 55 mm and a height of 70 mm, by agitating at a speed of 600 revolutions per minute with a magnetic agitator equipped with a 25 mm long magnetised bar, 2 g of polymer in 50 g of salty physiological solution and by measuring the time required for the vortex to disappear. In this test, the copolymers of the present invention require 50 to 80 seconds for the vortex to disappear.

The proportion of extractables is determined according to the following method:

1 g of the polymer to be tested is placed in 200 g of salty physiological solution;

this suspension is agitated for 16 hours at 20° C., then it is filtered;

the carboxylic and carboxylate functions present are analysed on 100 cm$^3$ of the filtrate;

the result of this analysis is expressed in grams of polymer dissolved for 100 g of dry polymer.

In this test, the copolymers of the present invention show a proportion of extractables of 1 to 5%. At the end of the polymerisation reaction, the reaction solvents are eliminated by azeotropic distillation until a suspension showing a proportion of dry content of 80±10% is obtained, then the suspension is filtered and the precipitate collected and dried to 90–95% dry content.

The absorption capacity by capillary action under a pressure of 15 g/cm$^2$ is determined at 20° C. according to the following protocol: 40 g of Fontainebleau sand with a granulometry of 0.1 to 0.3 mm, 2 g of copolymer to be tested and finally 40 g of Fontainebleau sand are spread successively and uniformly in a cylindrical funnel with a filtering plate of 90 mm in diameter and a porosity of 1. Then on the top layer of sand, using a glass disc of 90 mm diameter as an intermediary, a total load of 954 g is placed, then the funnel is plunged into a vat containing a salty physiological solution, at a constant level, in a manner so that the water level rigorously remains level with the upper face of the sintered glass and the quantity of salty physiological solution absorbed by the copolymer by capillary action in 90 minutes is measured.

The result is expressed in g of salty physiological solution per gram of dry polymer.

The dry extract is determined by drying a sample of constant weight at 140° C. and it is expressed in percentage by weight of dry product contained in the crude product.

The copolymers of the present invention therefore present interesting absorbent properties which justify their application as absorbing agents. Thus equally a subject of the invention is the polymers as defined previously, as absorbing constituents, preferably in an article of hygiene, notably for the manufacture of babies nappies, articles for incontinents or sanitary towels.

The following examples illustrate the invention without however limiting it:

EXAMPLE 1

In an inert atmosphere, 3.5 g of cellulose ethylether, containing from 48 to 49.5% of ethoxylated groups and showing at 25° C. a viscosity of 200 mPa.s determined in solution at 5% in a toluene-ethanol mixture 80–20 by weight, is dispersed in 618.5 g (7.35 moles) of cyclohexane.

In to this dispersion, carefully deoxygenated, agitated and maintained at boiling point, is introduced over 90 minutes, in an inert atmosphere, a solution obtained by extemporaneously mixing during the introduction of the following:
on the one hand a deoxygenated solution of:
  0.106 g of sodium peroxodisulphate,
  0.212 g of dicyano-4,4'-azo-4,4' dipentanoic acid dissolved in 10 g of 0.2N potash;
on the other hand, a solution prepared extemporaneously
  by dissolving at a temperature lower than 30° C.: 230 g (3.192 moles) of acrylic acid in 417.4 g of an aqueous solution of potash containing 128.9 g (2.297 moles) of potassium hydroxide,
  then by adding into this solution 319 mg of bis(oxiranylmethoxy)-1,4 butane. 1,4-butane.

The suspension obtained is then maintained for one hour at boiling point under agitation, then it is subjected to an azeotropic distillation with a recycling of the cyclohexane until the elimination of approximately 85% of the water present, and finally it is cooled down to ambient temperature and filtered. The precipitate collected is then dried at 110° C. for 60 minutes in a ventilated heating chamber. Thus a hydrophilic polymer is obtained in the form of white microbeads, insoluble in water, showing the following characteristics:
dry extract: 92%
water absorption capacity: 330 g per gram;
salty physiological solution absorption capacity:
  as is: 44 g/gram,
  under a pressure of 15 g/cm$^2$: 23 g/gram;
proportion of extractables: 2% by weight;
proportion of residual monomers: less than 0.005% by weight;
speed of absorption of a salty physiological solution: 70 s;
granulation: 0.1–0.8 mm.

EXAMPLE 2

Operating as in example 1 but using 208 mg instead of 319 mg of bis(oxiranylmethoxy)-1,4 butane.

A hydrophilic polymer is thus obtained, as microbeads, showing the following properties:
dry extract: 92%
water absorption capacity: 380 g/gram;
salty physiological solution absorption capacity:
  as is: 47 g/gram,
  under a pressure of 15 g/cm$^2$: 26 g/gram;
proportion of residual monomers: less than 0.005% by weight.

EXAMPLE 3

Operating as in example 1 but using 159 mg instead of 319 mg of bis(oxiranylmethoxy)-1,4 butane.

A hydrophilic polymer is thus obtained, as microbeads, showing the following properties:
dry extract: 92%
water absorption capacity: 485 g/gram;
salty physiological solution absorption capacity:
  as is: 54.5 g/gram,
  under a pressure of 15 g/cm$^2$: 27.5 g/gram;
proportion of extractables: 1.6%;
proportion of residual monomers: less than 0.005% by weight.

EXAMPLE 4

Operating as in example 1 but using 300 mg instead of 319 mg of bis(oxiranylmethoxy)-1,4 butane which is placed in the oil phase.

A hydrophilic polymer is thus obtained, as microbeads, showing the following properties:
dry extract: 92%;
water absorption capacity: 340 g/gram;
salty physiological solution absorption capacity:
  as is: 46.5 g/gram,
  under a pressure of 15 g/cm$^2$: 24 g/gram;
proportion of residual monomers: less than 0.005% by weight.

EXAMPLE 5

Operating as in example 1 but using 256 mg instead of 319 mg of bis(oxiranylmethoxy)-1,4 butane of which 128 mg are placed in the oil phase and 128 mg are placed in the aqueous phase containing the monomers.

A hydrophilic polymer is thus obtained, as microbeads, showing the following properties:
dry extract: 92%;
water absorption capacity: 320 g/gram;
salty physiological solution absorption capacity:
  as is: 46 g/gram,
  under a pressure of 15 g/cm$^2$: 27 g/gram;
proportion of residual monomers: less than 0.005% by weight.

It goes without saying that the present invention has been described only in a purely explanatory and in no way limiting manner and that any modification, in particular with regard to technical equivalence, can be made without being beyond its scope.

We claim:

1. Hydrophilic polymer, as microbeads, insoluble in water, based on acrylic acid and metal alkali acrylate, characterised in that it is constituted by an acrylic acid-potassium acrylate copolymer, containing in molar proportions from 55 to 85% of potassium acrylate, cross-linked with from 100 ppm to 3,000 ppm in relation to the total weight of monomers of one or more cross-linking agents chosen from the group constituted by the products of general formula 1:

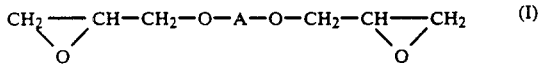

in which A represents a bivalent radical derived from a $C_3$-$C_6$ alkane, branched or not, by the removal of a hydrogen atom from each of the two terminal carbon atoms and that it shows a salty physiological solution absorption capacity of the order of 30 to 70 g per gram and of the order of 10 to 35 g per gram under a pressure of 15 g per cm$^2$.

2. Hydrophilic polymer according to claim 1, characterised in that it is cross-linked with 200 ppm to 3,000 ppm of 1,4-bis(oxiranylmethoxy)-butane.

3. Hydrophilic polymer according to claim 2, characterised in that it is cross-linked with 200 ppm to 1,000 ppm of 1,4-bis(oxiranylmethoxy)-butane.

4. Hydrophilic polymer according to claim 1 characterised in that it contains in molar proportions from 70 to 75% of potassium acrylate.

5. A hydrophilic polymer according to claim 2, comprising a molar proportion of potassium acrylate in the range of 70-75%.

6. A hydrophilic polymer according to claim 3, comprising a molar proportion of potassium acrylate in the range of 70-75%.

7. A hydrophilic polymer according to claim 1, comprising a molar proportion of potassium acrylate in the range of 65-80%.

8. A hydrophilic polymer, substantially insoluble in water and in the form of micro-beads having a salty physiological solution absorption capacity on the order of 30-70 g/g, said polymer being the reaction product of (1) an acrylic acid/potassium acrylate copolymer having a molar proportion of potassium acrylate of 65-80%, and (2) 200-3,000 ppm based on the total weight of monomers of a cross-linking agent of the formula

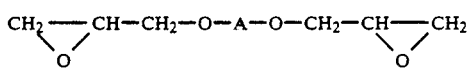

wherein A is a bivalent radical of a $C_3$-$C_6$ alkane from each terminal carbon atom of which a hydrogen atom has been removed.

9. A polymer according to claim 1 wherein A is selected from the group consisting of trimethylene, tetramethylene, ethylethylene, propylene and 2,2-dimethyl-1,3-propanediyl.

* * * * *